United States Patent [19]

Igaue et al.

[11] Patent Number: 5,080,658
[45] Date of Patent: Jan. 14, 1992

[54] DISPOSABLE ABSORBENT GARMENTS

[75] Inventors: Takamitsu Igaue, Kawanoe; Khoji Inoue, Ehime, both of Japan

[73] Assignee: Uni-Charm Corporation, Japan

[21] Appl. No.: 538,766

[22] Filed: Jun. 15, 1990

Related U.S. Application Data

[63] Continuation of Ser. No. 311,956, Feb. 17, 1989, abandoned.

[30] Foreign Application Priority Data

Feb. 19, 1988 [JP] Japan ................... 63-36604

[51] Int. Cl.⁵ .............................................. A61F 13/15
[52] U.S. Cl. ............................... 604/385.2; 604/385.1
[58] Field of Search ................... 604/385.1, 385.2, 394, 604/395, 396

[56] References Cited

U.S. PATENT DOCUMENTS

| | | | |
|---|---|---|---|
| 2,545,674 | 3/1951 | Ralph | 604/394 |
| 3,452,753 | 7/1969 | Sanford | 604/401 |
| 3,881,488 | 5/1975 | Delanty | 604/370 |
| 4,397,645 | 8/1983 | Buell | 604/385.2 |
| 4,578,071 | 3/1986 | Buell | 604/379 |
| 4,657,539 | 4/1987 | Hasse | 604/385.2 |
| 4,662,877 | 5/1987 | Williams | 604/385.1 |
| 4,695,278 | 9/1987 | Lawson | 604/385.1 |
| 4,704,115 | 11/1987 | Buell | 604/385.2 |
| 4,704,116 | 11/1987 | Enloe | 604/385.2 |
| 4,743,246 | 5/1988 | Lawson | 604/385.2 |
| 4,804,379 | 2/1989 | Toth | 604/385.1 |
| 4,808,177 | 2/1989 | DesMarais et al. | 604/385.1 |
| 4,808,178 | 2/1989 | Aziz et al. | 604/385.2 |
| 4,850,989 | 7/1989 | Villez | 604/385.2 |

FOREIGN PATENT DOCUMENTS

| | | | |
|---|---|---|---|
| 1512493 | 2/1968 | France | 604/386 |
| 0018031 | 8/1966 | Japan . | |
| 2159693 | 12/1985 | United Kingdom | 604/385.1 |
| 2161059 | 1/1986 | United Kingdom | 604/385.1 |

Primary Examiner—C. Fred Rosenbaum
Assistant Examiner—Sharon Finkel
Attorney, Agent, or Firm—Fred Philpitt

[57] ABSTRACT

Here is disclosed a disposable absorbent garment (such as disposable diaper) comprising a liquid-permeable topsheet, a liquid-impermeable backsheet, a liquid-absorbent core interposed between these sheets, side flaps comprising a first sheet and a second sheet and extending outwards from opposite side edges of the core, a first elastic member incorporated into each of the side flaps at a location adjacent the outer side edge of this side flap and a second elastic member also incorporated into each of the side flaps between the associated first elastic member and a location adjacent the associated side edge of the core wherein the second elastic member is affixed only to the first sheet so that a part of the first sheet occupied by the second elastic member rises into the user's skin as the second elastic member is allowed to contract.

4 Claims, 2 Drawing Sheets

DISPOSABLE ABSORBENT GARMENTS

This is a continuation of application Ser. No. 311,956, filed Feb. 17, 1989, now abandoned, and the benefits of 35 USC 120 are claimed relative to it.

BACKGROUND OF THE INVENTION

The present invention relates to disposable absorbent garments and particularly to articles such as disposable diapers, disposable pads against incontinence and disposable training pants all adapted to be placed around a crotch area of human body.

In disposable absorbent garments such as disposable diapers, the liquid-impermeable side flaps have conventionally been provided adjacent the outer side edges with the first elastic members and between the respective first elastic members and the respective side edges of the liquid-absorbent core with the second elastic members in order to assure an adequate sealing ability of said side flaps as disclosed in Patent Application Disclosure Gazette Nos. 62-250201 and 63-21901. According to such prior art, said second elastic members are affixed to the free ends of the respective second side flaps branched from the respective side flaps. Said second side flaps have their longitudinal ends fixedly folded in- or outwards.

The disposable diaper of another type is disclosed in Patent Application Disclosure Gazette No. 57-89602 and Utility Model Application Disclosure Gazette No. 62-88704 in which, in order to assure a reliable sealing effect, the elastic members affixed to the liquid-impermeable side flaps are configured to present the particular cross-sections so as to elastically urge the topsheet forming a part of each side flap as said elastic members are allowed to contract. Said particular cross-sections include inverted U-shape, O-shape and Ω-shape and these elastic members are joined to both the topsheet and the backsheet forming together each of said side flaps.

According to the prior art disclosed in said Patent Application Disclosure Gazette Nos. 62-250201 and 63-21901, the construction of each side flap becomes complicated and accordingly the article making process also becomes complicated, necessarily increasing a production cost, since the second side flaps are separately provided, to which the second elastic members are affixed and the longitudinal ends of said second side flaps are fixedly folded in- or outwards.

In accordance with the prior art disclosed in the previously mentioned Patent Application Disclosure Gazette No. 57-89602 and Utility Model Application Disclosure Gazette No. 62-88704, there is a problem in the operational efficiency with which the elastic members are affixed to the side flaps because of said particular cross-sections of said elastic members and the material cost necessarily increases since the elastic members must be relatively wide. Moreover, said elastic members are affixed to both the topsheet and the backsheet which form together said side flaps and the unique cross-sectional shapes of said elastic members are relied upon to urge the topsheet portions upwards. With a consequence, the height by which the topsheet portions can be urged upwards is disadvantageously limited by width and height(i.e., diametric dimension of the cross-section). Thus, the width and the cross-sectional diameter must be increased, even though this increases the material cost as mentioned above, in order to increase the height by which the topsheet portions can rise or can be urged upwards and thereby to improve the sealing effect.

SUMMARY OF THE INVENTION

A principal object of the present invention is to provide disposable absorbent garments by which the problems left unsolved by the previously described prior arts can be solved at once with a very simple countermeasure.

The present invention achieves this object by providing disposable absorbent garments comprising a liquid-permeable topsheet, a liquid-impermeable backsheet, a liquid-absorbent core interposed between said both sheets, liquid-impermeable side flaps respectively extending outwards from opposite side edges of said core, a first elastic member affixed to each of said side flaps adjacent outer side edge thereof, and a second elastic member affixed to each of said side flaps between said first elastic member and a location adjacent a side edge of said core, characterized in that: said side flap comprises a first sheet placed on a side destined to be in contact with the user's skin and a liquid-impermeable second sheet underlying said first sheet; said second elastic member is interposed between said first sheet and said second sheet and joined only to said first sheet; a first joining means located most closely to the inner side edge of said second elastic member to join said first sheet to a second sheet is spaced at least by 20 mm from a second joining means located most closely to the outer side edge of said second elastic member to join said first sheet to said second sheet; and thereby a part of said first sheet corresponding to a location of said second elastic member rises with respect to said first and second joining means serving as fulcrum, as said second elastic member is allowed to contract.

Said first sheet is air-permeable and liquid-impermeable, and preferably made of material different from that of said topsheet.

In this manner, when said article is put on, the portions of the side flaps occupied by said first and second elastic members are pressed against the user's skin under contractile force of said first and second elastic members, establishing an effective double seal between said portions and the user's skin. Particularly, the portions of said side flaps occupied by the second elastic members, namely, the first seal zones rise with respect to said first and second joining means serving as the fulcrum against the user's skin to establish the desired seal. It is effectively minimized thereby that excretion, particularly liquid contained therein might flow beyond this first seal zones established by rising of the topsheet portions towards the second seal zones provided by the first elastic members.

PREFERRED EMBODIMENT

The present invention will be described by way of example in reference with the accompanying drawing.

Figure 1:
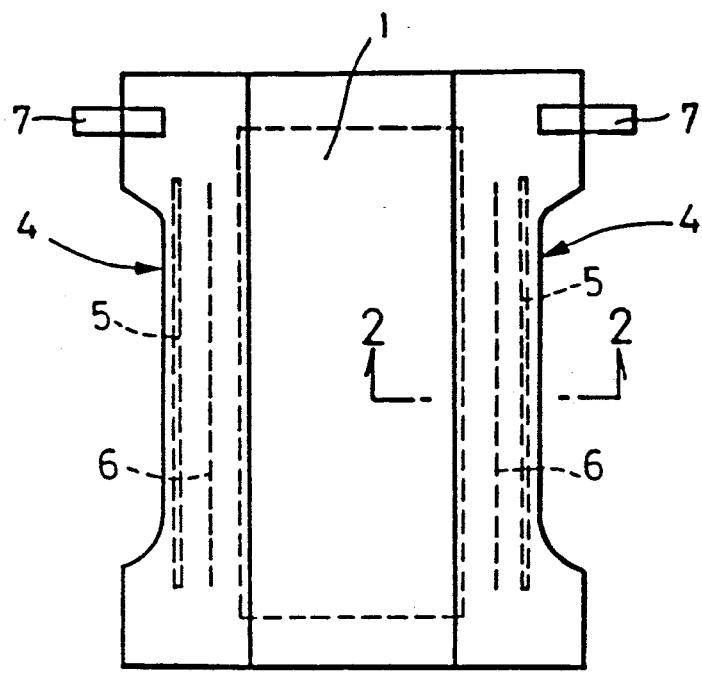
FIG. 1 is a developed plan view showing a disposable diaper as a specific example of articles according to the present invention.
Figure 2:
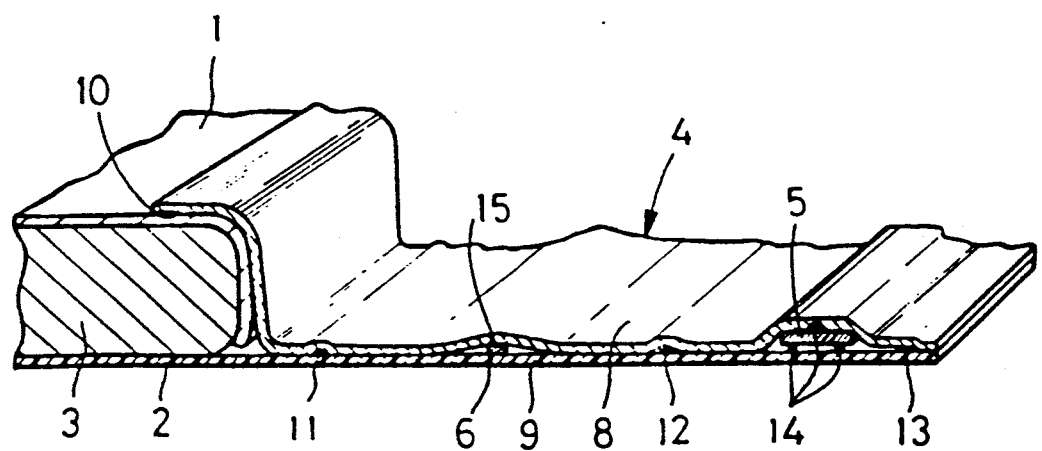
FIG. 2 is an enlarged fragmentary perspective view of said disposable diaper showing also a cross-section taken along a line II—II in FIG. 1.

FIGS. 1 and 2 illustrate a disposable diaper as a specific example of the disposable absorbent garments according to the present invention. The diaper comprises a liquid-permeable topsheet 1, a liquid-impermeable backsheet 2, a liquid-absorbent core 3 interposed between said both sheets, liquid-impermeable side flaps 4 respectively extending outwards from opposite side edges of said core, first and second elastic members 5, 6 incorporated into each of said side flaps so as to extend longitudinally of this side flap side-by-side at a predetermined distance from each other, and a tape fastener 7 affixed to each of said side flaps.

The side flap 4 is preferably porous but liquid-impermeable and comprises a first sheet 8 overlapping and extending outwardly from the topsheet 1 covering the top surface of the core 3 adjacent the associated side edge thereof and a portion 9 of the backsheet 2 (referred to hereinafter as a second sheet) extending outwardly from the associated side edge of the core 3 under said first sheet 8. Although it is preferable for prevention of leakage that the first sheet 8 overlaps the topsheet 1 so as to externally cover a portion of the core 3, the first sheet 8 may be placed under the topsheet 1 or may be placed to lie only upon the second sheet 9. Alternatively, the first sheet 8 may be joined along its inner side edge to the backsheet 2. It is also possible that the second sheet 9 is of material different from that of the backsheet 2 and then joined to said backsheet 2. The topsheet 1 is joined to the first sheet 8 and the first sheet 8 is joined to the second sheet 9 at least by longitudinally extending means 10, 11, 12, 13 for joining such as adhesive or welding. The first elastic member 5 is interposed between the first and second sheets 8, 9 adjacent outer side edges of these sheets and joined to these sheets by the joining means 14. The second elastic member 6 is interposed between the first and second sheets 8, 9 so as to lie substantially midway between the joining means 11, 12 and joined only to the first sheet 8 by the joining means 15.

Figure 3:
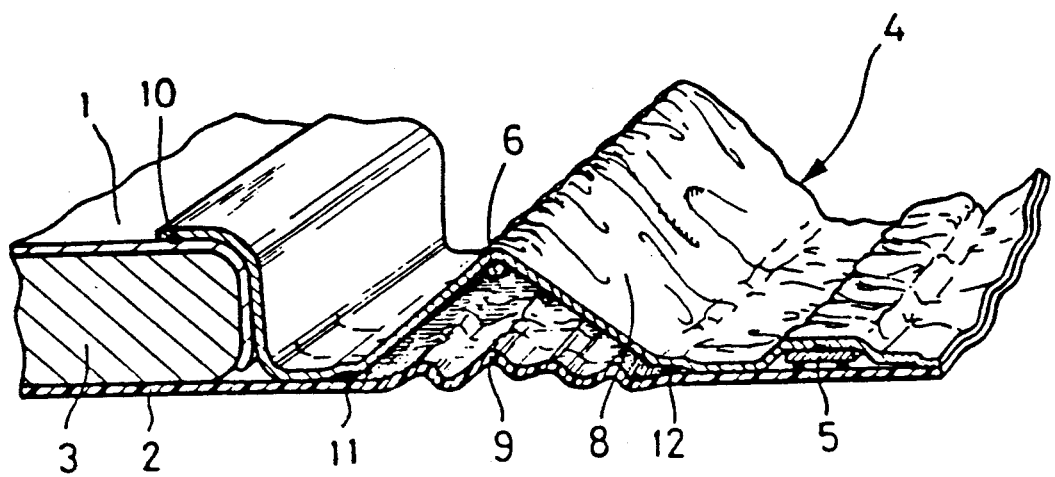
FIG. 3 is a view similar to FIG. 2 but showing how a side flap is deformed as the associated elastic member is allowed to contract.

Referring to FIG. 3, the first and second elastic member 5, 6 are shown as being allowed to contract. Because the first elastic member 5 is joined to both the first and second sheets 8, 9, a contractile force of said first elastic member 5 acts upon both said first and second sheets 8, 9, incurvating them upwards. A contractile force of the second elastic member 6 acts upon only the first sheet 8, since said second elastic member 6 is joined only to said first sheet 8, so that a portion of said first sheet 8 defined between the joining means 11, 12 rises on said joining means 11, 12 functioning as fulcrum in substantially an angular form with its apex corresponding to the location of said second elastic member 6. Such rising is preferably as high as possible and this height depends upon a distance between the joining means 11, 12 which are located most closely to said second elastic member 6. To obtain such rising of a desired height and thereby to achieve the object of the present invention, therefore, it is required to set said distance between the joining means 11, 12 to 20 mm or longer. Although the maximum value of this distance is not critical, it is generally preferable to limit said maximum value to 60 mm in view of a width of the side flap 4. Additionally, to improve the contractility of the second elastic member 6, distances from the inner and outer side edges of said second elastic member 6 to the joining means 11, 12 should be preferably at least 8 mm, respectively. The joining means which are closest to the second elastic member 6 may be located at, instead of the positions indicated by the reference numerals 11, 12, positions indicated by the reference numerals 10, 14. Width and cross-sectional shape of the individual second elastic member 6 as well as the number of the second elastic members 6 are not critical. However, it is preferred for achievement of said rising as high as possible under a restricted condition to concentrate the second elastic members 6 into a transverse range (width) as narrow as possible, if there are provided a plurality of the second elastic members 6, and it is preferred the second elastic member 6 is narrower as shown by FIG. 3, if there is provided the single second elastic member 6. In this manner, said rising has its apex being relatively acute and, as a result, said rising advantageously becomes higher. The first and second elastic members each has, in general, a contraction stress of 70 to 700 g and within this range the contraction stress of the second elastic member 6 may be higher of lower than that of the first elastic member 5. Specifically, even when the contraction stress of the second elastic member 6 itself is lower than the contraction stress of the first elastic member 5 itself, said second elastic member 6 can have a contraction stress substantially equivalent to the contraction stress of the first elastic member 5 without any significant restriction, since said second elastic member 6 is incorporated in the associated side flap 4 without being joined to the second sheet 9 and the distance between the joining means 11, 12 which are located most closely to said second elastic member 6 is at least 20 mm.

The topsheet 1 may be of nonwoven fabric, porous plastic film, etc., the backsheet 2 may be of plastic film (preferably porous waterproof film), laminate of said film and nonwoven fabric, etc., and the core 3 may be of fluffy pulp mixed with highly absorbent polymer particles etc.

The first sheet 8 forming a part of the side flap 4 may be preferably of a porous waterproof sheet such as melt bond nonwoven fabric composed of hydrophobic fibers, water-jet fiber entangled nonwoven fabric, such nonwoven fabric subjected to water repellent finish, or hydrophobic plastic film provided with fine porosity. It should be understood that the expression "porous(i.e., air-permeable)" used herein means an ability of 260 cc/cm$^2$ or higher as measured in accordance with the Japanese Industry Standard L 1004 and the expression "waterproof" means an ability of 20 mm or higher as measured in accordance with the JIS L 1092. The first sheet 8 preferably has a longitudinally rigidity of 10 to 80 mm as measured in accordance with the Clark's rigidity measuring method.

The first and second elastic members 5, 6 may be of stringy rubber, urethane rubber, urethane foam film, etc.

As will be apparent from the aforegoing description, the article constructed according to the present invention includes the first elastic member and the second elastic member both incorporated into each of the side flaps so as to be located at inner and outer zones of said side flap, respectively. Said second elastic member is joined only to the first sheet defining the upper surface of said side flap. And the distance between two means adapted to join said first sheet to the underlying sheet along lines longitudinally extending on opposite sides of said second elastic member so that the portion of said first sheet corresponding to the location of said second elastic member may sufficiently rise as said second elastic member is allowed to contract. In this way, a preventive effect for leakage of excretion equivalent to that achieved by the previously mentioned prior art without provision of second side flaps to which said second elastic members are respectively affixed or forming the cross-section of said second elastic member in a special shape as in the prior art. Unlike the prior art, the desired article can be produced with an extremely high productibility and supplied at a low cost, because the construction of the article is so simplified to require no special additional process.

Furthermore, said first sheet is porous(air-permeable) and liquid-impermeable, so the article according to the present invention is excellent in the preventive effect for excretion leakage as well as in the air-permeability, reducing a possible stuffiness inside the article.

What is claimed is:

1. A disposable absorbent garment comprising liquid-permeable top sheet (1), a liquid-impermeable back sheet (2), a liquid absorbent core (3) interposed between said sheets (1, 2), liquid-impermeable sideflaps (4) extending outwards from opposite side edges of said core, a first elastic member (5) within each of said sideflaps adjacent the outerside edge thereof, and a second elastic member (6) within each of said side flaps (4) at a location between said first elastic member (5) and said core (3):

said sideflap (4) comprising
      (a) a first sheet (8)
         that is bonded to said top sheet (1) but not a part thereof,
         that has an inner portion that overlaps both a portion of said top sheet (1) and a portion of said absorbent core,
         that is porous but liquid impermeable, and
         that is located on the side of flap (4) that is destined to be in contact with the user's skin, and
      (b) a second sheet (9) that is a continuation of said liquid-impermeable back sheet (2)
   said first sheet (8) and second sheet (9) being joined together by elongated joining lines, a first elongated joining line (11) being located on one side of said second elastic member (6) and a second elongated joining line (12) being located on the other side of said elastic member (6), said first and second elongated joining lines (11,12) being spaced apart from each other by a distance of at least 20 mm,
   said second elastic member (6) being interposed between said first sheet (8) and second sheet (9) and being affixed only to said first sheet (8);
   whereby the portion of said first sheet (8) that is affixed to said second elastic member (6) rises with respect to the portion of the second sheet (9) that extends between said first and second elongated joining means (11, 12) and functions as a fulcrum when said second elastic member (6) contracts.

2. A garment according to claim 1 wherein said second elastic member (6) has a contraction stress of 70 to 700 g.

3. A garment according to claim 1 wherein said first sheet (8) is air-permeable and liquid-impermeable, and made of a material different from that of said topsheet (1).

4. A disposable absorbent garment comprising liquid-permeable top sheet (1), a liquid-impermeable back sheet (2), a liquid absorbent core (3) interposed between said sheets (1, 2), liquid-impermeable sideflaps (4) extending outwards from opposite side edges of said core, a first elastic member (5) within each of said sideflaps adjacent the outerside edge thereof, and a second elastic member (6) within each of said sideflaps (4) at a location between said first elastic member (5) and said core (3):

said sideflap (4) comprising
      (a) a first sheet (8)
         that is bonded to said top sheet (1) but not a part thereof,
         that has an inner portion that overlaps both a portion of said top sheet (1) and a portion of said absorbent core,
         that is porous but liquid impermeable, and
         that is located on the side of flap (4) that is destined to be in contact with the user's skin, and
      (b) a second sheet (9) that is a continuation of said liquid-impermeable back sheet (2),
   said first sheet (8) and said underlying second sheet (9) being joined together by a plurality of elongated joining lines, that include at least one elongated joining line (10,11) located on the core side of said second elastic member (6) and at least one other elongated joining line (12) located on the side of said elastic member (6) away from said core, the elongated joining lines on opposite sides of said second elastic member being spaced apart from each other by a distance of at least 20 mm,
   said second elastic member (6) being interposed between said first sheet (8) and said underlying second sheet (9) and being affixed only to said first sheet (8);
   whereby the portion of said first sheet (8) that is affixed to said second elastic member (6) rises with respect to the portion of said underlying second sheet (9) that extends between said first and second elongated joining means (11, 12) and functions as a fulcrum when said second elastic member (6) contracts.

* * * * *